United States Patent
Spatz et al.

(10) Patent No.: US 8,257,798 B2
(45) Date of Patent: Sep. 4, 2012

(54) METHOD FOR THE CREATION OF EXTENSIVE VARIATIONS IN SIZE OR DISTANCE IN NANOSTRUCTURE PATTERNS ON SURFACES

(75) Inventors: Joachim P. Spatz, Stuttgart (DE); Theobald Lohmueller, Nuremberg (DE); Marco Arnold, Gaiberg (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 358 days.

(21) Appl. No.: 12/595,507

(22) PCT Filed: Mar. 12, 2008

(86) PCT No.: PCT/EP2008/001981
§ 371 (c)(1),
(2), (4) Date: Dec. 10, 2009

(87) PCT Pub. No.: WO2008/125172
PCT Pub. Date: Oct. 23, 2008

(65) Prior Publication Data
US 2010/0112234 A1 May 6, 2010

(30) Foreign Application Priority Data
Apr. 11, 2007 (DE) .......................... 10 2007 017 032

(51) Int. Cl.
*H05H 1/00* (2006.01)
*G01N 1/00* (2006.01)
(52) U.S. Cl. ........ 427/535; 427/2.11; 427/404; 424/423
(58) Field of Classification Search .................. None
See application file for complete search history.

(56) References Cited

U.S. PATENT DOCUMENTS
5,891,366 A 4/1999 Gruenwald et al.
(Continued)

FOREIGN PATENT DOCUMENTS
CA 2308302 * 5/1999
(Continued)

OTHER PUBLICATIONS
Lengl et al., Excimer laser ablation of gold-loaded inverse polystyrene-block-poly(s-vinylpyridine) micelles, Appl. Phys. A 72, 679-685 (2001).*
(Continued)

*Primary Examiner* — Michael Cleveland
*Assistant Examiner* — Francisco Tschen
(74) *Attorney, Agent, or Firm* — Caesar, Rivise, Bernstein, Cohen & Pokotilow, Ltd.

(57) ABSTRACT

A method for creating extensive variations in size or distance in nanostructure patterns on surfaces preferably includes: a) contacting a substrate with a liquid phase containing organic two-block or multi-block copolymer micelles, which are charged with an inorganic metal compound, by immersion into this liquid phase, during which chemically different polymer domains including inorganic metal compounds enclosed in micelles are deposited on the substrate; b) withdrawing the substrate from the liquid phase at a predetermined withdrawing speed, which is varied continuously or gradually, so that a gradient of the lateral separation length of the polymer domains is produced on the substrate surface; c) converting the deposited inorganic metal compounds by an oxidation- or reduction treatment into inorganic nanoparticles and optionally complete or partial removal of the organic polymer by a plasma treatment, wherein positions and lateral separation length of the nanoparticles obtained are determined by those of deposited polymer domains.

21 Claims, 8 Drawing Sheets

U.S. PATENT DOCUMENTS

| | | |
|---|---|---|
| 2002/0145132 A1 | 10/2002 | Won et al. |
| 2005/0059760 A1 | 3/2005 | Dellwo et al. |

FOREIGN PATENT DOCUMENTS

| | | |
|---|---|---|
| DE | 19747815 A1 | 5/1999 |
| EP | 1027157 B1 | 8/2000 |
| WO | 9921652 A3 | 5/1999 |

OTHER PUBLICATIONS

Meltzer et al., Fabrication of Nanostructures by Hydroxylamine Seeding of Gold Nanoparticle Templates, Langmuir 2001, 17, 1713-1718.*

Efimenko et al., "How to Prepare Tunable Planar Molecular Chemical Gradients", Adv. Mater., vol. 13 (2001), pp. 1560-1563.

Glass et al., "Block copolymer micelle nanolithography", Nanotechnology, vol. 14 (2003), pp. 1153-1160.

Gorzolnik et al., "Nano-structured micropatterns by combination of block copolymer self-assembly and UV photolithography", Nanotechnology, vol. 17 (2006), pp. 5027-5032.

Hahn et al., "Graphoepitaxial Deposition of Cationic Polymer Micelles on Patterned SiO2 Surfaces", Langmuir, vol. 20 (2004), pp. 1489-1494.

Kastle et al., "Micelle Nanoreactors—Preparation and Characterization of Hexagonally Ordered Arrays of Metallic Nanodots", Adv. Funct. Mater., vol. 13 (2003), pp. 853-861.

Kronholz et al., "Self-Assembly of Diblock-Copolymer Micelles for Template-Based Preparation of PbTiO3 Nanograins", Adv. Funct. Mater., vol. 16 (2006), pp. 2346-2354.

Meiners et al., "Adsorption of Block-Copolymer Micelles from a Selective Solvent", Macromolecules, vol. 30 (1997), pp. 4945-4951.

Moller et al., "Ordering and Packing Periodicity of Au-Containing Block Copolymer Micelles", Polymeric Materials: Science & Engineering, vol. 90 (2004), pp. 255-256.

Poondi et al., "Synthesis of Silver Nanoparticles by a Laser-Liquid-Solid Interaction Technique", Journal of Materials Synthesis and Processing, vol. 6 (1998), pp. 89-104.

Spatz et al., "Functional nanostructures by organized macromolecular-metallic hybrid systems", Journal of Luminescence, vols. 76&77 (1998), pp. 168-173.

Spatz et al., "Micellar Inorganic-Polymer Hybrid Systems—A Tool for Nanolithography", Adv. Mater., vol. 11 (1999), pp. 149-153.

Zhou et al., "Scanning thermal microscopy and atomic force microscopy studies of laser-induced deposited metal lines", Applied Surface Science, vol. 120 (1997), pp. 149-158.

* cited by examiner

METHOD FOR THE CREATION OF EXTENSIVE VARIATIONS IN SIZE OR DISTANCE IN NANOSTRUCTURE PATTERNS ON SURFACES

BACKGROUND OF THE INVENTION

The preparation of chemical and topographic variations on the nano- and micrometer scale are, i.a., of great technical interest for usages in the areas of refractive and diffractive optics, the selection of molecularly important length scales in the cellular adhesion and the bonding of individual molecules on boundary surfaces. This is true in particular for gradual changes of the topography and chemical properties of a surface.

The production of molecularly well-defined gradients offers, e.g., the possibility of investigating directionally controlled processes such as the cell movement that requires external chemical gradients. In particular in the area of cellular haptotaxis chemical gradients with molecular precision are desirable for investigating biological reactions qualitatively and quantitatively in detail. Efimenko and Genzer ((Adv. Mater. 13, 2001), 1560-1563) have shown that a fine positioning of the graft density of molecules on surfaces is possible by the creation of mechanically assembled monolayers (MAMs). MAMs are structures that are produced by a combination of self-assembly, mechanical stretching of a PDMS carrier and molecular diffusion. The method for the production of these MAMs is relatively complex due to the incorporation of a mechanical step and furthermore only suitable for flexible carriers and not for rigid substrates such as, e.g., glass, metal, silicon compounds, etc. Another disadvantage is the fact that a regulation of molecule-molecule distance by mechanical stretching of a substrate is not possible since the clustering of individual molecules cannot be substantially limited.

Accordingly, the present invention has the object of providing an improved, simple and versatile method with which extensive variations in size or distance can be so precisely adjusted in nanostructure patterns on surfaces that defined gradient surfaces are obtained.

This object was achieved in accordance with the invention by a further development of the micellar nanolithography (see, e.g., EP 1 027 157). In the micellar nanolithography a micellar solution of a block copolymer is deposited onto a substrate, e.g., by immersion coating, and, given suitable conditions on the surface, forms an ordered film structure of chemically different polymer domains, depending, i.a., on the type, molecular weight and concentration of the block copolymer. The micelles in the solution can be charged with inorganic salts that can be reduced to inorganic nanoparticles after the deposition with the polymer film. It was now established in accordance with the invention that the lateral separation length of said polymer domains and therewith also of the resulting nanoparticles as well as the size of these nanoparticles can be so precisely adjusted in an extensive area by different measures that nanostructured surfaces with desired gradients of distance and/or size can be created.

Thus, the present invention has as subject matter methods for the extensive variation of sizes or distances in patterns of nanostructures on a substrate.

SUMMARY OF THE INVENTION

As already mentioned, the present invention is based on the further development of the technology of micellar nanolithography (see, e.g., EP 1 027 157). In the micellar nanolithography a micellar solution of a diblock- or multiblock copolymer is deposited onto a substrate, e.g., by immersion coating, and, given suitable conditions on the surface, forms an ordered film structure of chemically different polymer domains, depending, i.a., on the type, molecular weight and concentration of the block copolymer. For example, the distances of the individual polymer domains from each other are a function of the molecular weight and the concentration of the block polymer in the solution. The micelles in the solution can be charged with inorganic salts or acids that can be reduced to inorganic nanoparticles after the deposition with the polymer film.

It was now established according to the invention that the lateral separation length of said polymer domains and therewith also of the resulting nanoparticles as well as the size of these nanoparticles can be adjusted so precisely in an extensive area that nanostructured surfaces can be created with desired gradients of distance and/or size.

An essential step in the development of the present invention was the recognition that a fine adjustment of the lateral separation length of the deposited polymer domains and/or of the resulting nanoparticles is made possible for the creation of gradient surfaces by the variation of the withdrawing speed at which the substrate to be coated is withdrawn from a micellar solution.

It had already been observed by Moller et al., (Polym. Mat., Science and Engineering, 2004, 90, 255) that the degree of order as well as the distances of nanostructures that had been produced by the micellar nanolithography were a function of the (constant) withdrawing speed with which a mica substrate was drawn from the micellar solution. However, considering the observed, relatively strong variation of the degree of order with the withdrawing speed under a few tested conditions, these first experimental results let the creation of a separation length gradient with the necessary precision and the necessary degree of order appear unrealistic and this was also neither discussed nor suggested therein. In particular, a molecular weight distribution between the blocks PS and P2VP was also used there that is unsuited for a controlled change of the distance between the micelles. An Mw (PS)>>Mw (P2VP) is desirable herein.

The evaluation of extensive tests with different micellar solutions described here in which the same substances were drawn with different yet constant withdrawal speeds (see example 2) yielded two important results. In the first place, a range of almost linear decrease of the distances with higher withdrawing speeds was able to be obtained for all tested solutions, and in the second place, the degree of order of the nanostructures varied with the withdrawing speed, but nevertheless could be held high by selecting suitable polymers and polymer concentrations. This led to the conclusion that it should be possible to also produce a gradient of the lateral separation length of the polymer domains and/or nanoparticles on the substrate surface by gradual variation of the withdrawing speed at which a substrate surface is drawn from a micellar solution.

Accordingly, the method of the invention for the extensive variation of sizes or distances in patterns of nanostructures on a substrate comprises in one embodiment a) Contacting a substrate with a liquid phase that contains micelles of an organic two-block- or multi-block copolymer, which micelles are charged with an inorganic metal compound (e.g. a metallic salt), by immersion into this liquid phase, during which chemically different polymer domains comprising inorganic metal compounds (e.g., metallic salts) enclosed in micelles are deposited on the substrate;

b) Withdrawing of the substrate from the liquid phase at a predetermined withdrawing speed, which withdrawing speed is varied continuously or gradually, so that a gradient of the lateral separation length of the polymer domains is produced on the substrate surface; and c) Conversion of the inorganic metal compounds in the deposited polymer domains by an oxidation- or reduction treatment into inorganic nanoparticles and optionally complete or partial removal of the organic polymer by a plasma treatment, wherein the positions and lateral separation length of the nanoparticles obtained are determined by the positions and the lateral separation length of the deposited polymer domains.

The withdrawing speed in step b) is typically varied continuously or gradually in a range of 0.1 mm/min to 100 mm/min, preferably 1 mm/min to 20 mm/min.

The method can be carried out, for example, in such a manner that an abrupt, gradual change of speed takes place in a phase of relatively low continuous change of speed. In this manner, e.g., several different separation length gradients can be produced in series on the same substrate surface.

Basically any micelle-forming block copolymer can be used as two-block or multi-block copolymer in this method that can be deposited as a film onto a substrate and that forms an ordered structure of different polymer domains. Suitable block copolymers are, for example, all block copolymers mentioned in the above-cited EP 1 027 157. In a more specific embodiment the two-block- or multi-block copolymer is selected from the group of polystyrene (n)-b-poly (2-vinylpyridine (m), polystyrene (n)-b-poly (4-vinylpyridine (m), polystyrene (n)-b-poly (ethylene oxide) (m), in which n and m indicate the number of repetition units and are, independently of one another, integers in the range of 10-10,000, in particular 100-1000. The molecular weight (Mw) (dissolved block) is preferably selected >>Mw (poorly dissolved block).

Basically all inorganic metal compounds (e.g., metallic salts) that can be converted by oxidation or reduction into inorganic nanoparticles are suitable as inorganic compounds with which the micelles in the solution and the polymer domains in the deposited plastic film, respectively, can be charged. Suitable salts are, for example, all metallic salts mentioned in the above-cited EP 1 027 157. The metallic salts used in accordance with the invention preferably comprise at least one salt of the metals Au, Pt, Pd, Ag, In, Fe, Zr, Al, Co, Ni, Ga, Sn, Zn, Ti, Si or Ge. $HAuCl_4$ is especially preferred.

In a specific embodiment of the method in accordance with the invention the reductive conversion of the metal compounds in the polymer domains deposited on the substrate surface into nanoparticles takes place in step c) by irradiation with a light field intensity-modulated laterally along the substrate surface, as a result of which differently sized nanoparticles are produced as a function of the light intensity at different positions of the substrate surface.

After or simultaneously with the conversion of the metal compounds into inorganic nanoparticles the organic polymer can be entirely or partially removed by an appropriate treatment. This treatment is typically a plasma treatment, e.g., with an oxygen- or hydrogen plasma as known in the state of the art. More detailed data about such a treatment can also be found, e.g., in EP 1 027 157.

Figure 1A:
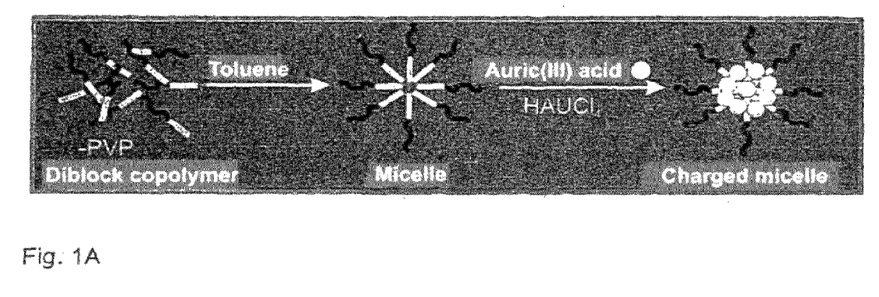
FIG. 1A schematically shows the formation of a micelle from a PS-PVP diblock copolymer and the charging with a gold (III) compound.
Figure 1B:
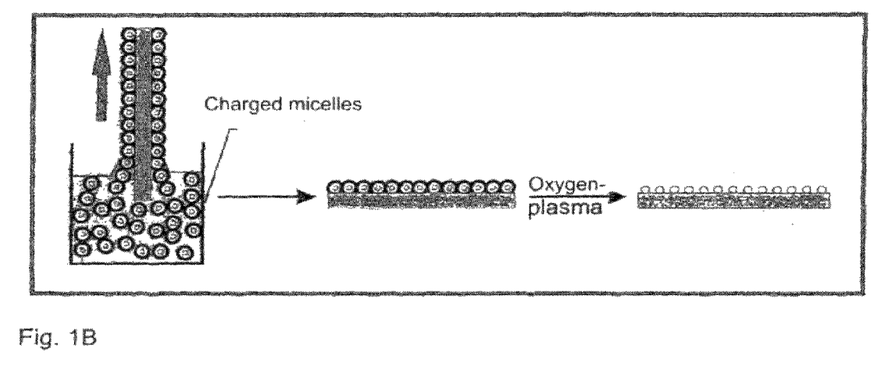
FIG. 1B schematically shows the application of charged micelles on a substrate and the later removal of the polymer film by a plasma treatment.
Figure 2:
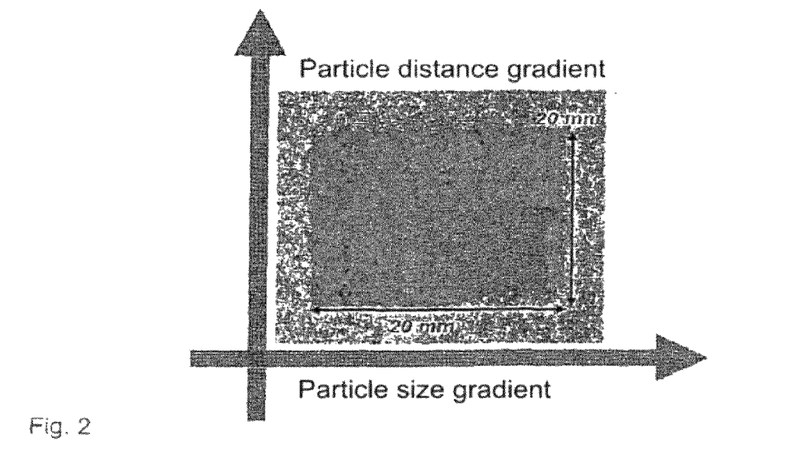
FIG. 2 shows a photograph of a twofold gradient of gold nanoparticles.
Figure 3:
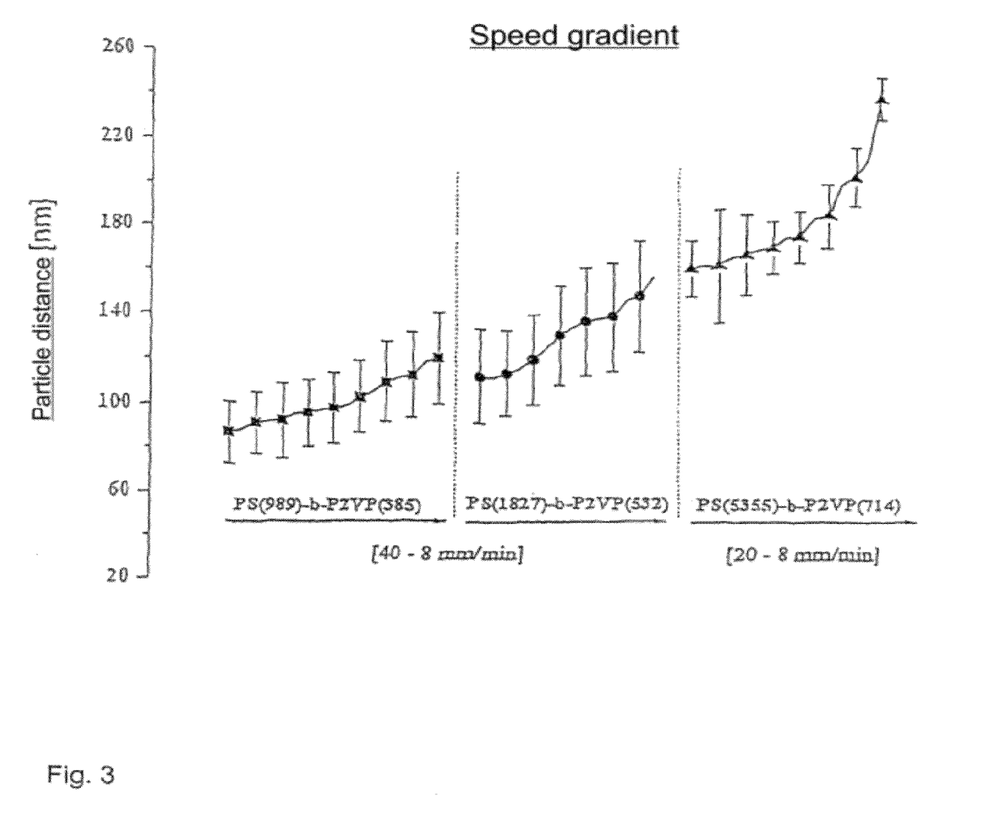
FIG. 3 shows the variation of the particle distance as a function of the withdrawing speed of a substrate from a micellar solution.
Figure 4:
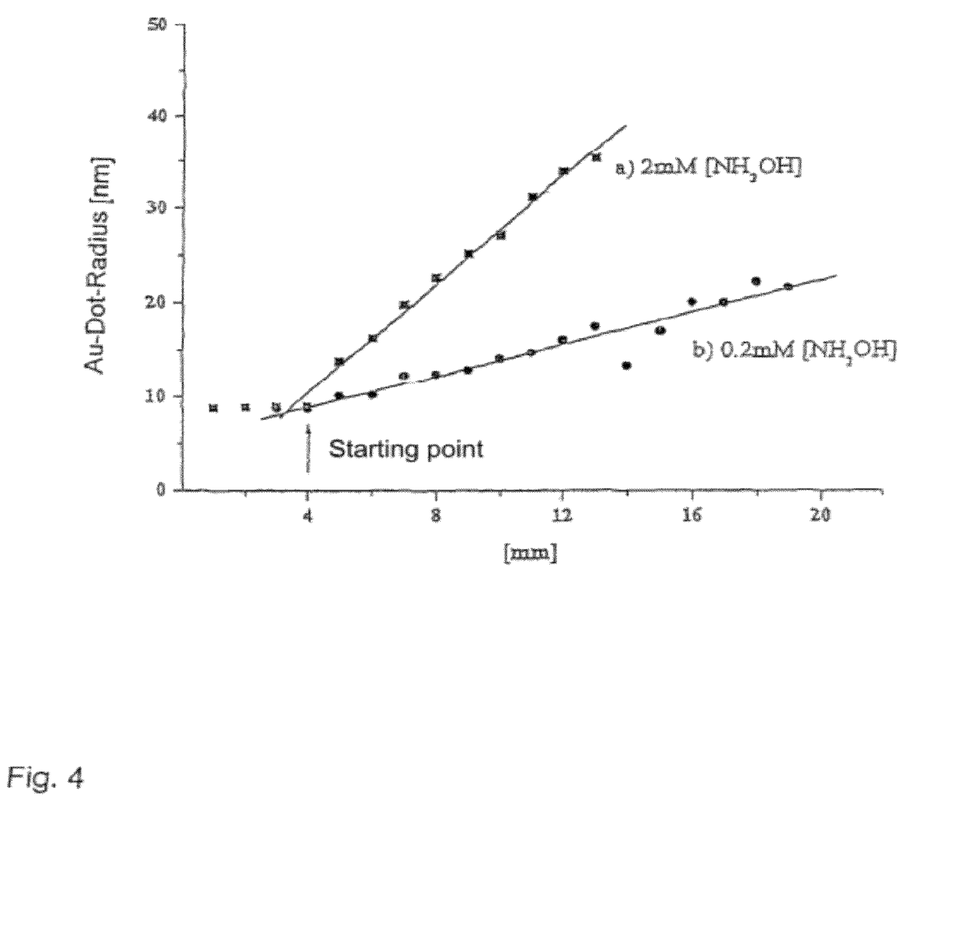
FIG. 4 shows the variation of the particle size as a function of the position on a substrate.
Figure 5:
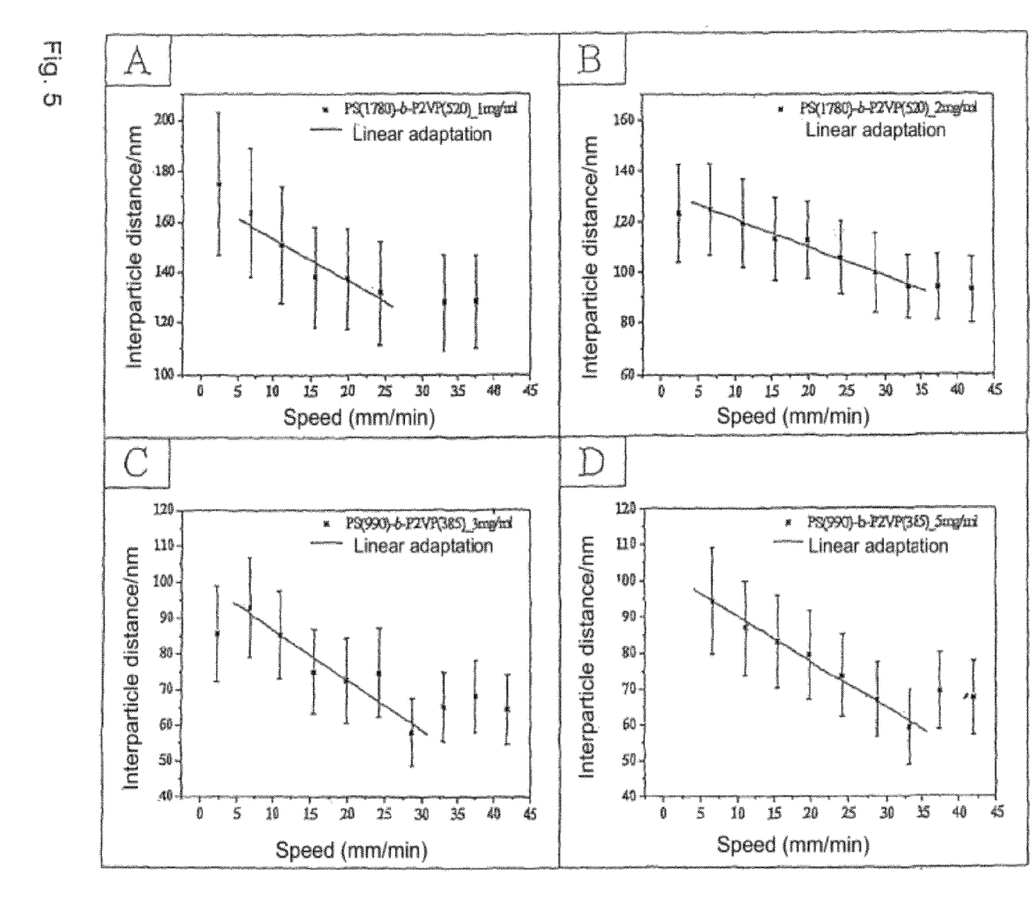
FIG. 5A-D show the mean Au gold particle separation lengths obtained at different withdrawing speeds for different copolymer solutions A-D.

In a more specific embodiment of the method in accordance with the invention, the method further comprises the following steps:

d) Contacting of the substrate with the nanoparticles obtained according to step c) with a liquid phase containing a solution of an inorganic metal compound (e.g., $HAuCl_4$ in 0.01-10 mM $NH_2OH$) by immersion into this liquid phase, during which dissolved material grows on the nanoparticles and thus enlarges them; and e) Withdrawing the substrate from the liquid phase after a predetermined time period, as a result of which a desired size of the nanoparticles is adjusted (see, e.g., FIG. 4).

A gradient of the particle size can also be produced on the substrate surface during the above by a variation of the withdrawing speed in step e). The particle size can be adjusted here within a range of approximately 1-200 nm at a length >100 μm.

The withdrawing speed is typically continuously or gradually varied in step e) within a range of 0.1 mm/min to 100 mm/min, preferably of from 1 mm/min to 20 mm/min.

In a more specific embodiment of this method the nanoparticles are irradiated on the substrate surface during the steps d) and e) with a light field intensity-modulated laterally along the substrate surface, as a result of which differently sized nanoparticles are produced at different positions of the substrate surface on account of the differing growth speed of the nanoparticles that is a function of the light intensity. The wavelength is approximately 120-500 nm and the light intensity can vary according to requirement over a broad range from very small to very large.

A gradient of the particle size can also be produced by the irradiation with an intensity-modulated light field. The particle size can be finely adjusted here within a range of approximately 1-200 nm at a length >0.3 μm.

In a preferred embodiment of the method in accordance with the invention several of the above-described measures are carried out simultaneously or sequentially so that at least one separation length gradient as well as at least one particle size gradient of the nanoparticles is produced on a nanostructured substrate surface.

A further aspect of the present invention is a method for the production of nanoparticles with a laterally variable size on a substrate surface, in which a polymer film containing at least one inorganic metal compound (e.g., a metallic salt) is deposited on a substrate surface and is then irradiated with a light field laterally intensity-modulated in an extensive area, as a result of which the metallic salt is reduced and converted into nanoparticles and the size of the nanoparticles at a certain position of the substrate surface is a function of the intensity of the light field at this position.

In this manner a gradient of the particle size can be produced on the substrate surface.

The polymer film is preferably deposited on the substrate surface in such a manner that an ordered structure of polymer domains containing metallic salt is produced with a certain lateral separation length, which separation length determines the separation length of the nanoparticles after the conversion of the metal compounds into nanoparticles. In a more specific embodiment of this method the polymer film is deposited in such a manner that a separation length gradient of polymer domains is produced on the substrate surface.

The substrate with the deposited polymer film is preferably subjected after the irradiation with light to a plasma treatment, e.g., with oxygen- or hydrogen plasma, that entirely or partially degrades the polymer.

In a more specific embodiment of this method the substrate surface with the formed nanoparticles is subsequently introduced into a liquid phase containing a solution of a metal compound, during which dissolved material grows on the nanoparticles and thus enlarges them, and the substrate is withdrawn from the liquid phase after a predetermined time period, as a result of which a desired size of the nanoparticles is adjusted.

In the above method variants in which an irradiation with intensity-modulated light is carried out, the intensity of the light field can be adjusted gradually or in stages by interference and diffraction on static or dynamically variable optical elements. A typical apparatus for this comprises, e.g., the following components: light source, mirrors, interference grid, diffractive optical elements. The latter can be actuated in a pattern-active manner in the case of liquid crystals or micromirrors and thus be actively (dynamically) affected with respect to their interference properties.

DETAILED DESCRIPTION OF PREFERRED EMBODIMENTS

The following examples serve for the more detailed illustration of the present invention without, however, limiting the same thereto.

EXAMPLE 1

Distance Variation of Gold Nanoparticles by the Use of Different Constant Speeds for Withdrawing the Substrate from a Micellar Solution Different solutions A, B, C and D were produced whose characteristics are summarized in the following Table 1.

TABLE 1

| Micellar solution | Polymer | L = $HAuCl_4/P2VP$ | Polymer conc. (mg/ml) |
|---|---|---|---|
| A | PS(1780)-b-P2VP(520) | 0.2 | 1 |
| B | PS(1780)-b-P2VP(520) | 0.2 | 2 |
| C | PS(990)-b-P2VP(385) | 0.3 | 3 |
| D | PS(990)-b-P2VP(385) | 0.3 | 5 |

These solutions were produced by dissolving the particular block copolymer in the provided concentration in dry toluene and subsequent addition of $HAuCl_4 \times H_2O$ in the indicated ratio L, and the mixture was agitated until the tetrachloroauric acid had been completely solubilized.

For each solution 10 samples (glass slides) were carefully cleaned, e.g., with "piranha" solution ($H_2O_2/H_2SO_4$=1:1), dried with pure water, dried in a flow of nitrogen and immersed in the particular micellar solution and withdrawn at different speeds. After a hydrogen-plasma treatment (e.g., as described in EP 1 027 157) the gold nanoparticle distances were determined with the scanning electron microscope. To this end 5 different areas were analyzed on each glass slide (20×20 mm) at an enlargement of 5000.

In order to calculate the particular mean interparticle distances and the standard deviations the computer analysis program Origin 7.0 was used. The 5 nanoparticle-separation values obtained with their particular standard deviations were averaged in order to determine the mean total interparticle distances for a single slide that was drawn from the solution of the diblock copolymer for each of the 10 different withdrawing speeds.

TABLE 2

| Micellar solution | Minimal interparticle distance (nm) + Standard deviation | Minimal interparticle distance (nm) ± Standard deviation | A (nm) |
|---|---|---|---|
| A | 128 ± 18 | 175 ± 28 | 47 |
| B | 93 ± 13 | 125 ± 18 | 32 |
| C | 58 ± 9 | 93 ± 14 | 35 |
| D | 59 ± 9 | 94 ± 14 | 35 |

FIG. 5A-D shows all tested solutions and the particular corresponding interparticle distances at each withdrawing speed. This study demonstrated that in all tested solutions an almost linear decrease of the distances with higher withdrawing speeds was able to be obtained. The maximal difference in the lateral distancing of the gold nanoparticles for the tested solutions was approximately 40 nm. It is noteworthy that at a certain speed the distancing of the gold nanoparticles seems to experience a saturation. On the other hand a decrease of the pattern order was observed at a very low speed (2.3 mm/min) that led to sharply differing interparticle distances at different measuring positions on the substrate.

Figure 6:
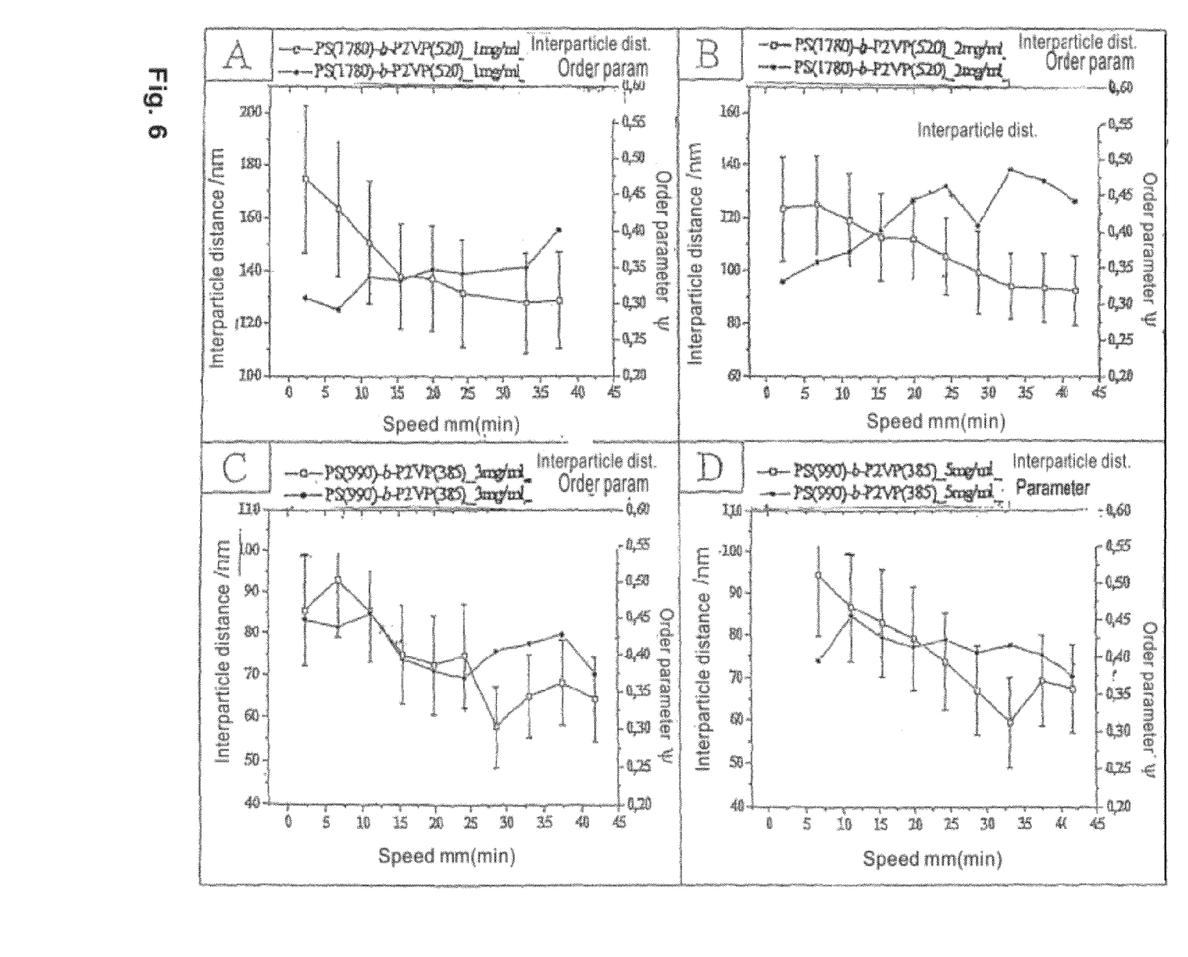
FIG. 6 shows the correlation between the order parameter, the interparticle differences and the withdrawing speeds for these solutions A-D.

FIG. 6 shows the correlation between the order parameter, the interparticle differences and the withdrawing speeds. The solutions A and B showed an elevation of the order parameter with increasing speed whereas the order parameter remained constant or slightly decreased when the withdrawing speed in solutions C and D was raised. Obviously, too low a micelle density on the surface (e.g., on account of too low a polymer concentration or too low a withdrawing speed) results in a lower degree of order on the surface and it can be concluded that there is an optimal micelle density in a monomicellar layer regarding the pattern quality for each diblock copolymer.

EXAMPLE 2

Separation Length Gradients of Gold Nanoparticles by Variation of the Withdrawing Speed of the Substrate out of a Micellar Solution In this experiment three samples with gradients of 1 mm, 2 mm and 3 mm length were produced. The variation of the withdrawing speed from the micellar solution, produced analogously to example 1, varied from 40 mm/min ("initial speed") to 8 mm/min ("final speed").

The substrates were moved with an electromotor whose withdrawing speed was adjustable via the programmable voltage of its energy supply.

TABLE 3

| | Polymer | L = $HAuCl_4$/ P2VP | Polymer conc. (mg/ml) | Gradient length (mm) | Slope (nm/mm) |
|---|---|---|---|---|---|
| Gradient 1 | PS(990)-b-P2VP(385) | 0.3 | 3 | 1 | 21 ± 9 |
| Gradient 2 | PS(990)-b-P2VP(385) | 0.3 | 3 | 2 | 10 ± 6 |
| Gradient 3 | PS(990)-b-P2VP(385) | 0.3 | 5 | 3 | 7 ± 4 |

Figure 7:
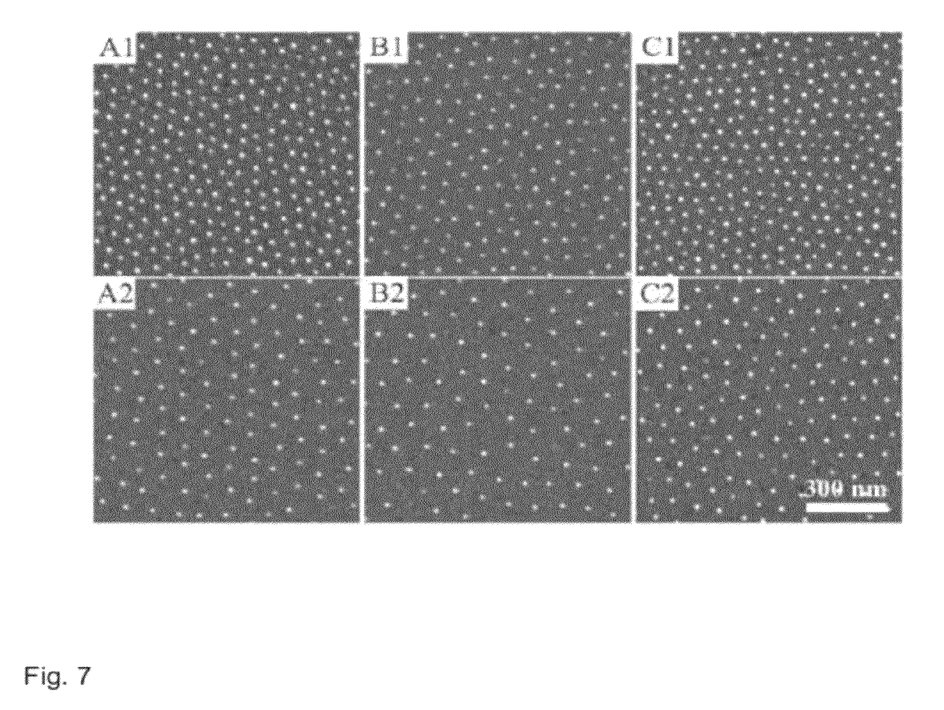
FIG. 7 shows representative scanning electron microscope photographs of the nanopatterns obtained from different separation length gradients at a position at the start of the gradient as the substrate was withdrawn at a high withdrawing speed from the corresponding block copolymer solution (A1, B1, C1) and at a position at the end of the gradient with a low withdrawing speed (A2, B2, C2).

FIG. 7 shows scanning electron microscope photographs of the nanopatterns obtained from each gradient substrate at a position at the start of the gradient as the substrate was withdrawn at 40 mm/min withdrawing speed from the corresponding block copolymer solution (A1, B1, C1), and at a position at the end of the gradient with a withdrawing speed of 8 mm/min (A2, B2, C2) (A gradient 1; B gradient 2; C gradient 3). The scanning electron microscope photographs demonstrate that no adverse effect on the gold nanopatterns can be detected when a single substrate is withdrawn at the indicated different speeds.

Figure 8:
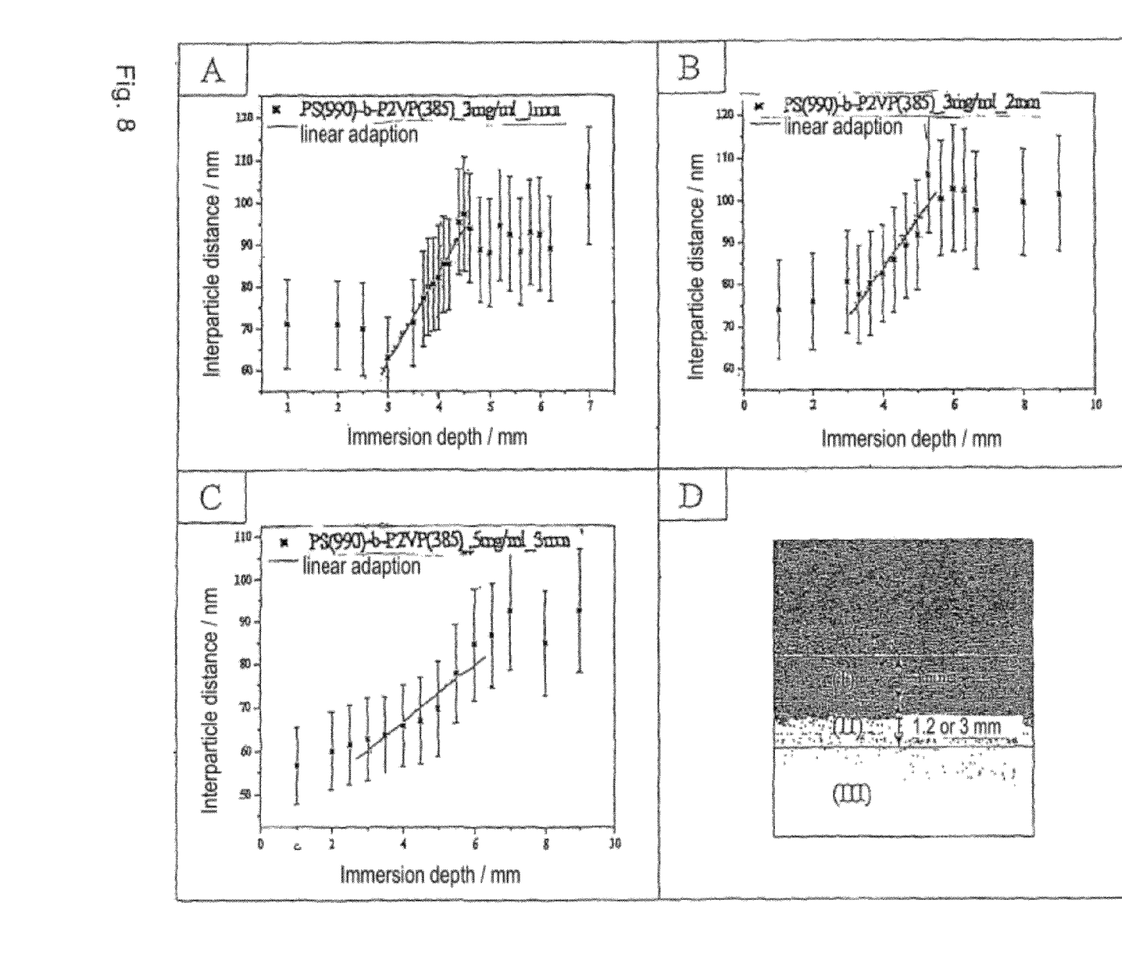
FIG. 8 shows the interparticle distances (FIG. 8A-C) measured along the gradients and the shape of the gradients (FIG. 8D).

FIG. 8 shows the interparticle distances measured along the gradients (FIG. 8A-C) and the shape of the gradients (FIG. 8D). It is apparent from FIG. 8A-C that an almost linear increase of the interparticle distances occurred, which is to be ascribed to the linear decrease of the withdrawing speed. This means that steeper slopes were obtained for shorter gradient lengths. The slope of a gradient is indicated by the ratio of the gradient length to the increase of the interparticle distances. All gradients started and ended at positions that were predetermined by a computer program.

EXAMPLE 3

Production of Several Separation Length Gradients on a Substrate

In this experiment two different gradients were produced on a substrate. For this, the withdrawing speed for the first gradient was elevated from 8 to 40 mm/min and reduced for the second gradient from 40 to 8 mm/min.

TABLE 4

Properties of two conversely oriented gradients

| | Polymer | L = $HAuCl_4$/ P2VP | Polymer conc. (mg/ml) | Gradient length (mm) | Slopes (nm/mm) 1 | 2 |
|---|---|---|---|---|---|---|
| Gradient 4 | PS(1780)-b-P2VP(520) | 0.2 | 2 | 3 | −11 ± 5 | +11 ± 5 |
| Gradient 5 | PS(990)-b-P2VP(385) | 0.3 | 3 | 1 | −31 ± 8 | 23 ± 9 |

Figure 9:
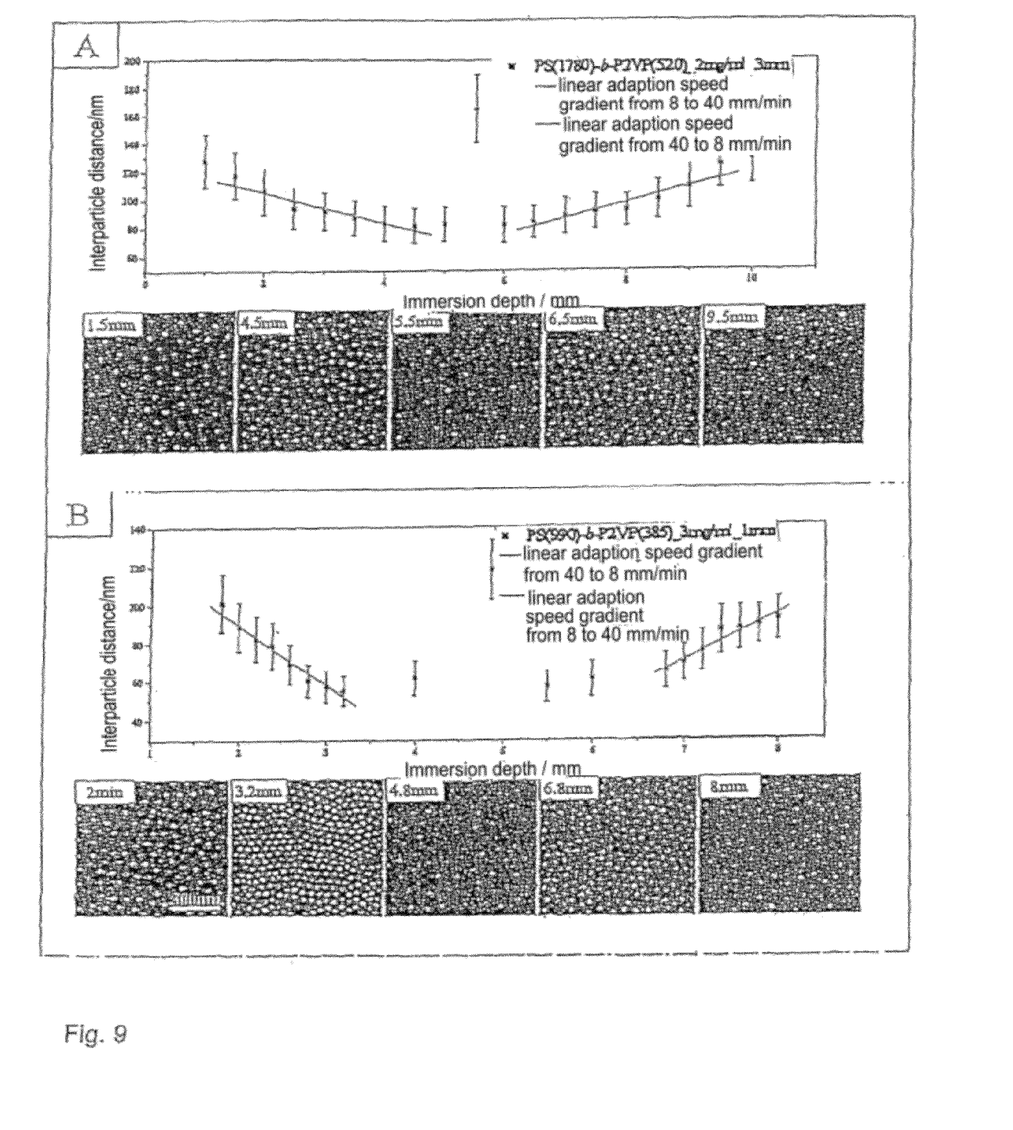
FIG. 9 indicates the interparticle distances of two conversely oriented gradients on a substrate as plot against the immersion depth and shows scanning electron microscope photographs of different positions on each substrate.

FIG. 9 indicates the interparticle distances of these conversely oriented gradients as plots against the immersion depth (corresponds to the gradient length) and shows scanning electron microscope photographs of different positions on each substrate.

The determination of the interparticle distances yielded results that were comparable to those of individual gradients. These results provide evidence that a gradient formation in both directions was possible by varying the withdrawing speed. The unusually high interparticle distances that were observed in the middle of the substrate can be explained by the sudden stop at 0/min from a speed of 40 μm/min and can be considered as areas that were withdrawn at very low speed.

EXAMPLE 4

Particle Size Gradients of Gold Nanoparticles by Variation of the Withdrawing Speed A relatively steep particle gradient of 10-40 nm on a stretch of approximately 13 mm (2 mM [$NH_2OH$]) and a flatter particle gradient of approximately 10-25 nm (0.2 mM [$NH_2OH$]) on a stretch of approximately 15 mm was produced by variation of the withdrawing speed from 0.01 to 100 mm/min of an already nanostructured glass platelet from solutions with the following composition: a) aqueous 2 mM $NH_2OH$+1 mg/m $HAuCl_4$, b) aqueous 0.2 mM $NH_2OH$+1 mg/m $HAuCl_4$ (see FIG. 4).

EXAMPLE 5

Superpositioning of a Particle Gradient with a Perpendicular Separation Length Gradient At first a separation length gradient is produced on a substrate in accordance with Example 2, then the substrate is rotated through 90° and a particle gradient produced in analogy with Example 4.

The invention claimed is:
1. A method for variation of sizes or distances in patterns of nanostructures on a substrate, comprising
   a) contacting a substrate with a liquid phase that contains micelles of an organic two-block- or multi-block copolymer, said micelles being charged with an inorganic metal compound, by immersion into the liquid phase, during which chemically different polymer domains comprising metal compounds enclosed in micelles are deposited on the substrate;
   b) withdrawing of the substrate from the liquid phase at a predetermined withdrawing speed, which withdrawing speed is varied continuously or gradually, so that a gradient of a lateral separation length of the polymer domains is produced on a substrate surface;
   c) conversion of the metal compounds in the deposited polymer domains by an oxidation- or reduction treat- ment into inorganic nanoparticles and optionally complete or partial removal of the organic copolymer by a plasma treatment, wherein positions and a lateral separation length of the nanoparticles obtained are determined by positions and a lateral separation length of the deposited polymer domains.

2. The method according to claim 1, wherein the withdrawing speed in step b) is varied in a range of 0.1 mm/min to 100 mm/min.

3. The method according to claim 2, wherein the withdrawing speed is changed abruptly and gradually in a phase of relatively low continuous change of speed such that several different separation length gradients are produced in series on the same substrate surface.

4. The method according to one of claim 1, wherein the reductive conversion of the metal compounds in the polymer domains deposited on the substrate surface into nanoparticles takes place in step c) by irradiation with a light field intensity-modulated laterally along the substrate surface, as a result of which differently sized nanoparticles are produced as a function of the light intensity at different positions of the substrate surface.

5. The method according to claim 4, wherein a gradient of the particle size is produced by the irradiation with an intensity-modulated light field.

6. The method according to claim 4, further comprising the following steps:
   d) contacting of the substrate with the nanoparticles obtained according to step c) with a liquid phase containing a solution of an inorganic metal compound by immersion into the liquid phase, during which dissolved material grows on the nanoparticles and thus enlarges the nanoparticles; and
   e) withdrawing the substrate from the liquid phase after a predetermined time period, as a result of which a desired size of the nanoparticles is adjusted.

7. The method according to claim 6, wherein the nanoparticles are irradiated on the substrate surface during the steps d) and e) with a light field intensity-modulated laterally along the substrate surface, as a result of which differently sized nanoparticles are produced at different positions of the substrate surface on account of a differing growth speed of the nanoparticles that is a function of the light intensity.

8. The method according to claim 4, wherein the intensity of the light field is adjusted gradually or in stages in an extensive area by interference and diffraction on static or dynamically variable optical elements.

9. The method according to claim 1, further comprising the following steps:
   d) contacting of the substrate with the nanoparticles obtained according to step c) with a liquid phase containing a solution of an inorganic metal compound by immersion into the liquid phase, during which dissolved material grows on the nanoparticles and thus enlarges the nanoparticles; and
   e) withdrawing the substrate from the liquid phase after a predetermined time period, as a result of which a desired size of the nanoparticles is obtain.

10. The method according to claim 9, wherein a gradient of the particle size is produced on the substrate surface by variation of the withdrawing speed in step e).

11. The method according to claim 9, wherein the nanoparticles are irradiated on the substrate surface during the steps d) and e) with a light field intensity-modulated laterally along the substrate surface, as a result of which differently sized nanoparticles are produced at different positions of the substrate surface on account of a differing growth speed of the nanoparticles that is a function of the light intensity.

12. The method according to claim 11, wherein a gradient of the particle size is produced by the irradiation with an intensity-modulated light field.

13. The method according to claim 12, wherein at least one separation length gradient as well as at least one particle size gradient of the nanoparticles is produced on a nanostructured substrate surface.

14. The method according to claim 11, wherein the intensity of the light field is adjusted gradually or in stages in an extensive area by interference and diffraction on static or dynamically variable optical elements.

15. The method according to claim 1, wherein the inorganic metal compound comprises at least one salt of the metals selected from the group consisting of Au, Pt, Pd, Ag, In, Fe, Zr, Al, Co, Ni, Ga, Sn, Zn, Ti, Si and Ge.

16. The method according to claim 1, wherein the two-block- or multi-block copolymer is a member selected from the group consisting of polystyrene (n)-b-poly(2-vinylpyridine(m), polystyrene(n)-b-poly(4-vinylpyridine(m), and polystyrene (n)-b-poly(ethylene oxide)(m), in which n and m indicate a number of repetition units and are, independently of one another, integers in a range of 10-10,000.

17. A method for producing nanoparticles with a laterally variable size on a substrate surface, wherein a polymer film containing at least one inorganic metal compound is deposited on a substrate surface and is then irradiated with a light field laterally intensity-modulated in an extensive area, as a result of which the metal compound is reduced and converted into nanoparticles and the size of the nanoparticles at a certain position of the substrate surface is a function of an intensity of the light field at the position, and wherein a nanoparticle size gradient is produced on the substrate surface.

18. The method according to claim 17, wherein the substrate with the deposited polymer film is subjected after the irradiation with light to a plasma treatment that entirely or partially degrades the polymer.

19. The method according to claim 17, wherein the substrate surface with the formed nanoparticles is subsequently introduced into a liquid phase containing a solution of an inorganic metal compound, during which dissolved material grows on the nanoparticles and thus enlarges them, and the substrate is withdrawn from the liquid phase after a predetermined time period, as result of which a desired size of the nanoparticles is adjusted.

20. A method for producing nanoparticles with a laterally variable size on a substrate surface, wherein a polymer film containing at least one inorganic metal compound is deposited on a substrate surface and is then irradiated with a light field laterally intensity-modulated in an extensive area, as a result of which the metal compound is reduced and converted into nanoparticles and the size of the nanoparticles at a certain position of the substrate surface is a function of an intensity of the light field at the position, wherein the polymer film is deposited on the substrate surface in such a manner that an ordered structure of polymer domains containing metal compound(s) is produced with a certain lateral separation length, said lateral separation length determining the separation length of the nanoparticles after the conversion of the metal compounds into nanoparticles, and wherein a separation length gradient of polymer domains is produced on the substrate surface.

21. A method for producing nanoparticles with a laterally variable size on a substrate surface, wherein a polymer film containing at least one inorganic metal compound is deposited on a substrate surface and is then irradiated with a light field laterally intensity-modulated in an extensive area, as a result of which the metal compound is reduced and converted into nanoparticles and the size of the nanoparticles at a certain position of the substrate surface is a function of an intensity of the light field at the position, and wherein the intensity of the light field is adjusted gradually or in stages in an extensive area by interference and diffraction on static or dynamically variable optical elements.

* * * * *